(12) United States Patent
Conrad et al.

(10) Patent No.: US 10,266,426 B1
(45) Date of Patent: Apr. 23, 2019

(54) UV WATER TREATMENT IN PORTABLE WATER TANK

(71) Applicant: MAG Aerospace Industries, LLC, Carson, CA (US)

(72) Inventors: David Eugene Conrad, Lakewood, CA (US); Razmik B. Boodaghians, Glendale, CA (US); Roger Michael Wilbanks, Cerritos, CA (US); Garen Bowen Murray, Provo, UT (US)

(73) Assignee: MAG Aerospace Industries, LLC, Carson, CA (US)

(*) Notice: Subject to any disclaimer, the term of this patent is extended or adjusted under 35 U.S.C. 154(b) by 0 days.

(21) Appl. No.: 15/835,077

(22) Filed: Dec. 7, 2017

(51) Int. Cl.
*A61L 2/10* (2006.01)
*C02F 1/32* (2006.01)
*C02F 103/00* (2006.01)

(52) U.S. Cl.
CPC ............... *C02F 1/325* (2013.01); *A61L 2/10* (2013.01); *C02F 2103/008* (2013.01); *C02F 2201/001* (2013.01); *C02F 2201/3222* (2013.01); *C02F 2201/3225* (2013.01); *C02F 2201/3227* (2013.01); *C02F 2303/04* (2013.01)

(58) Field of Classification Search
CPC .. C02F 1/325; C02F 1/002; C02F 1/32; C02F 2303/04; C02F 2201/3222; A61L 2/10; A61L 9/20; Y02A 20/214; A23L 3/28; A61N 5/06; A61N 5/0624
USPC ....... 250/423 R, 432, 455.11, 504 R, 453.11, 250/461.1, 492.1; 210/764; 422/186.3
See application file for complete search history.

(56) References Cited

U.S. PATENT DOCUMENTS

| | | | |
|---|---|---|---|
| 6,058,718 A * | 5/2000 | Forsberg | C02F 9/005 62/125 |
| 6,463,956 B2 * | 10/2002 | Walker | E03B 7/04 137/563 |
| 6,776,822 B2 | 8/2004 | Johnson | |
| 7,666,317 B2 * | 2/2010 | Hsueh | B08B 9/0321 210/206 |
| 7,981,285 B2 | 7/2011 | Thorpe | |
| 8,816,300 B1 * | 8/2014 | Walker | C02F 1/325 210/192 |
| 8,872,130 B1 * | 10/2014 | Matthews | C02F 1/325 250/455.11 |
| 9,061,923 B2 | 6/2015 | Hsueh | |
| 9,260,323 B2 | 2/2016 | Boodaghians | |
| 2002/0074559 A1 * | 6/2002 | Dowling | A61N 5/06 257/99 |
| 2004/0222163 A1 * | 11/2004 | Saccomanno | A61L 2/10 210/748.11 |
| 2005/0139552 A1 * | 6/2005 | Forsberg | E03B 3/28 62/635 |
| 2007/0131872 A1 | 6/2007 | Shearer et al. | |

(Continued)

OTHER PUBLICATIONS

Europe Patent Application No. 18210585.8, Extended European Search Report, dated Feb. 14, 2019.

*Primary Examiner* — David A Vanore
(74) *Attorney, Agent, or Firm* — Kilpatrick Townsend & Stockton LLP; Dean W. Russell; Kristin M. Crall

(57) ABSTRACT

Systems and methods for treating and disinfecting water contained in a potable water tank. The systems and methods generally use one or more UV LEDs that are positioned along various portions of the water tank and that are configured to emit UV light/irradiation into the water contained therein.

11 Claims, 5 Drawing Sheets

(56) References Cited

U.S. PATENT DOCUMENTS

| | | | |
|---|---|---|---|
| 2009/0261264 A1* | 10/2009 | Hormann | C02F 1/325 250/373 |
| 2010/0155339 A1* | 6/2010 | Gunter | C02F 1/325 210/739 |
| 2012/0011874 A1* | 1/2012 | Conradt | C02F 1/325 62/264 |
| 2012/0051977 A1* | 3/2012 | Boodaghians | C02F 1/325 422/117 |
| 2013/0146783 A1* | 6/2013 | Boodaghians | C02F 1/325 250/435 |
| 2014/0017135 A1* | 1/2014 | Boodaghians | A61L 9/205 422/121 |
| 2014/0102965 A1* | 4/2014 | Jones | C02F 1/002 210/136 |
| 2014/0353256 A1* | 12/2014 | Kaschek | C02F 9/00 210/663 |
| 2015/0034545 A1* | 2/2015 | Park | C02F 1/003 210/251 |
| 2015/0102235 A1* | 4/2015 | Lee | A61L 2/10 250/492.1 |
| 2015/0129776 A1* | 5/2015 | Boodaghians | C02F 1/325 250/432 R |
| 2015/0158741 A1* | 6/2015 | Lee | C02F 1/003 210/184 |
| 2015/0217984 A1* | 8/2015 | Orita | B67D 1/0004 222/95 |
| 2015/0314024 A1* | 11/2015 | Khan | C02F 1/325 250/435 |
| 2015/0344329 A1* | 12/2015 | Smetona | C02F 1/325 250/437 |
| 2016/0107904 A1* | 4/2016 | Rajagopalan | C02F 1/325 250/432 R |
| 2016/0289090 A1* | 10/2016 | Liao | C02F 1/325 |
| 2018/0086649 A1* | 3/2018 | Hayashi | C02F 1/325 |

* cited by examiner

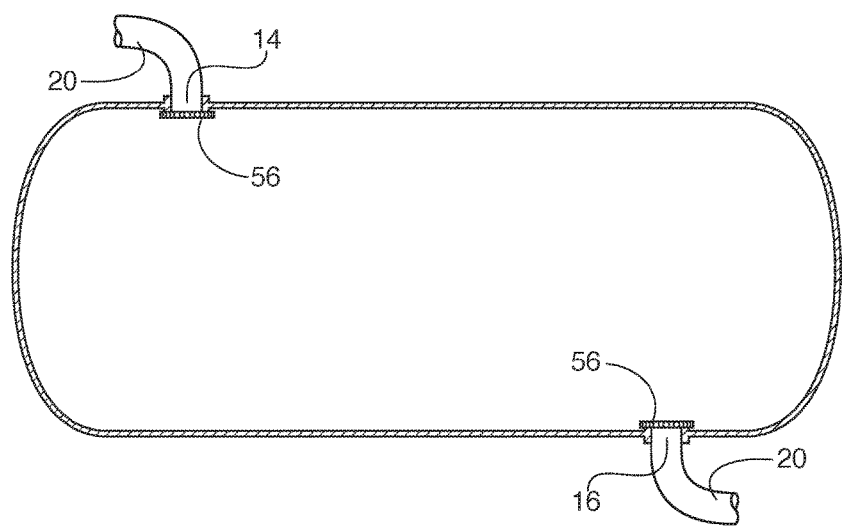
FIG. 9
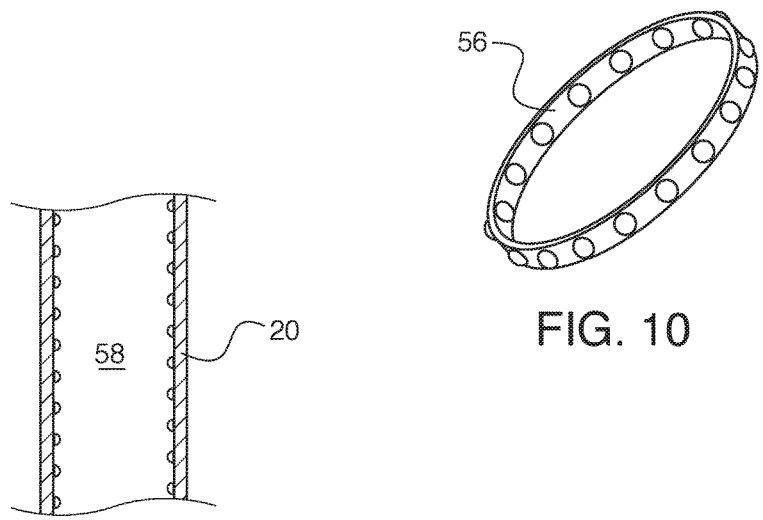
FIG. 10
FIG. 11

UV WATER TREATMENT IN PORTABLE WATER TANK

FIELD OF THE DISCLOSURE

Embodiments of the present disclosure relate generally to an ultraviolet (UV) light disinfection system for a water tank. One or more UV light emitting diodes (LEDS) are positioned in the water tank in order to expose the water contained therein to germicidal light treatment.

BACKGROUND

Disinfection of water on-board passenger transportation vehicles is necessary to guarantee water quality. This may include disinfection of potable water that is held in a self-contained potable water tank onboard the vehicle. The water held in the tank is ultimately intended for delivery to beverage makers, sinks for hand-washing, toilets for flushing, or is otherwise routed on-board the vehicle for various forms of use or consumption such as humidifier. As one example, water systems on aircraft are complicated systems that usually include a tank with plumbing conduits and a pressurization system to deliver water to the various points of use.

The issue of water quality, and in particular, of potable water quality, on passenger transportation vehicles and equipment, such as aircraft, trains, boats and ships, and the like is a point of interest for regulatory authorities. Regulatory standards have been enacted that require water carried on-board passenger vehicles to meet certain standards such as the US EPA Aircraft Drinking Water Rule. Passenger airlines and other transportation companies must thus meet the relevant drinking water standard. If failing to do so, the aircraft water system has to go through disinfection process per specified protocol and retested, accordingly. This can lead to the aircraft being grounded until retesting of water quality and confirmation that the water management system is free of any microbial contamination.

Airlines and other passenger transport vehicle companies must ensure that the potable water (i.e., drinkable water) carried aboard the aircraft is fit for human consumption by employing appropriate disinfection protocols and prevent cross-contamination during water upload. Disinfection upon upload and periodic disinfection sampling does not always adequately address the issue of contamination that may occur in the water tank and/or when the water is leaving the tank for use on board the aircraft. For example, air must periodically be introduced into the water storage and dispensing system on the aircraft in order to maintain pressurization, as well as to drain the system during routine servicing. This air can introduce airborne pathogens or bacteria that can multiply and cause unsanitary conditions and unacceptable water quality in the intervals between samplings or disinfection procedures. In effect, because the water storage and dispensing system is routinely exposed to the outside environment, potable water quality inside the water holding tank cannot always be ensured without some form of additional treatment. Additionally, water storage tanks are often drained at the end of the flight in order to prevent water freezing or other bacterial buildup. Because the internal surface of the water supply tank is then subjected to moist air from many hours until the surface dries, this can also be a breeding ground for microorganisms or other biofilms.

Specifically, microorganisms and biofilms may contaminate water held in a self-contained potable water supply, such as water tanks located onboard passenger transportation vehicles. Accumulation may occur along the interior surfaces of the water tank. It is also possible for bacteria, viruses, spores, mold, algae, or other microorganisms to grow in contaminated water holding tanks. The moist metal or plastic interior surfaces of the water tank in a light absence setting may provide a prime breeding area for microorganism biofilms that may build up and slough off into the water. There is thus a need to further disinfect the water that is held in the water tank on an on-going basis, not only upon upload or its delivery to its point of use.

Chlorination or other chemical treatment is not always effective in reducing or removing bacteria lying beneath a protective biofilm. On the other hand, ultraviolet (UV) light treatment can eliminate bacteria, viruses, spores, and mold in the water. It can purify water by making biological impurities inactive. Ultraviolet lamps are generally designed to destroy the links in these micro-organisms' DNA so that they are de-activated and cannot reproduce. The crucial hydrogen bonds that link the DNA chain together rupture when exposed to light between the wavelengths of about 220 nm to about 310 nm. In a particular example, the range may be from about 250-270 nm. In an even more particular example, there may be a single mono wavelength of 254 nm.

There are a number of water treatment solutions being employed and/or studied for use on-board aircraft. For example, one way that water can be treated is via UV mercury lamps. These lamps deliver an ultraviolet light to the water in the system and have been found beneficial because the treatment does not change the taste or odor of the water, it kills bacteria, viruses and protozoan, it is compact and easy to use, and it can prevent biofilm if the system is kept clean. However, one of the disadvantages of mercury UV lamps for water treatment is that they require a medium to high electrical demand, which means that when used on-board a vehicle such as an aircraft, they pull electrical power from the aircraft engines and/or an auxiliary power unit (APU). Increased usage of aircraft power from the engines results in higher fuel consumption and costs. Other disadvantages are that UV mercury lamps require cleaning and new lamps annually, and if a mercury lamp is broken, there exists a chance for mercury contamination of the water to be treated. Additionally, UV lamps take a while to power on if not in constant use. For UV lamps, the highest peak is generally mono-chromatic, in that the lamps generally only emit one effective wavelength, which is usually 254 nm for water treatment.

A further method of water treatment that has been explored is the use of ultraviolet light emitting diode (UV LED) light for water treatment. In addition to the mercury lamp benefits, the use of UV LED light also has the advantage of being able to use a wider UV band with multiple LED wavelengths, and it can offer a high power output with less power consumption than UV lamps. UV LEDs have greater longevity, power up quickly without requiring a delay time built into the system for the UV light source to reach its optimum UV energy output, and do not contain mercury. There are not currently available systems that are designed for use on-board a transportation vehicle such as aircraft that are imbedded and/or part of the tank water structural design.

Therefore, a current need exists for a UV LED system for use in a vehicle or aircraft environment that can deliver appropriate UV treatment to water contained and being held in an onboard potable water tank. The present assignee owns patents related to point of use water treatment (U.S. Pat. No. 9,260,323), to water treatment upon upload (U.S. Pat. No.

9,061,923), and to chemical water treatment (U.S. Pat. No. 7,666,317). However, it has been determined desirable to provide a system that can be installed within the water holding tank on board a vehicle. Some companies provide water treatment units that recirculate water from the tank through the unit, returning the water to the tank during flight. However, the problem of direct in-tank water treatment has not been adequately solved to date.

BRIEF SUMMARY

Embodiments described herein thus provide systems and methods for treating and disinfecting water contained in a potable water tank. These systems generally use one or more UV LEDs that are positioned along various portions of the water tank and that are configured to emit UV light/irradiation into the water contained therein.

BRIEF DESCRIPTION OF THE DRAWINGS

FIG. 9 shows one example of a UV treatment system installed at the inlet and outlet of a water tank.

FIG. 10 shows an example of a UV LED ring.

FIG. 11 shows an example of a UV LED sheath.

DETAILED DESCRIPTION

Figure 1:
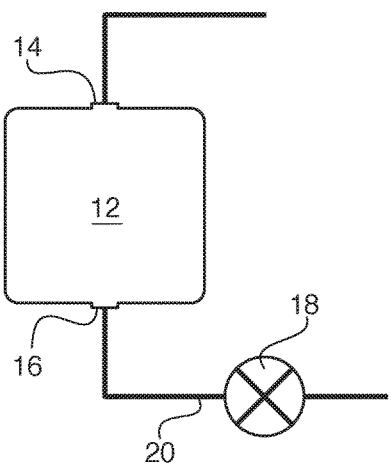
FIG. 1 shows a schematic view of a water tank.

The disclosed potable water tank treatment system 10 is configured for use onboard a passenger vehicle. As illustrated by FIG. 1, the potable water tank treatment system 10 includes a water tank 12 in fluid communication with a recirculation system or a series of water conduits 20 or other method for moving the water out of the water tank and throughout the vehicle for end use. There is typically provided an inlet 14 for water delivery into the water tank and an outlet 16 that is configured to deliver water away from the tank 12, through the series of water conduits 20. A pump 18, such as a recirculating pump or other pump system, may be provided that pumps water out of the tank 12 and to its end use location. In other examples, the water may leave the tank via pressure from a compressed airline, via gravity, via vacuum pull, or via any other appropriate exit system. It is relevant to note that the pump 18 is not required for disinfection using the present system, because the disinfection takes place inside the water tank 12. This is in contrast to prior art systems that treat water recirculating through the entire water system (in the water conduits 20 themselves) or at one or more points of use or points of entry.

The water treatment system 10 described in generally uses one or more UV LEDs (ultraviolet light emitting diodes) in order to disinfect water held within the water tank 12. Applicants have realized a number of benefits that may be achieved by using UV LEDs rather than traditional UV bulbs and/or mercury lamps. For example, as compared mercury lamp benefits, the use of UV LED light provides the advantage of being able to use a wider UV band with multiple LED wavelengths. It can also offer a high power output with less power consumption than UV lamps. UV LEDs have greater longevity, power up quickly without requiring a delay time built into the system for the UV light source to reach its optimum UV energy output, and do not contain mercury. Some companies have been manufacturing UV lamps and LED systems for water sanitation and disinfection, but none of the available systems are designed for use on-board a transportation vehicle or an aircraft, nor are they designed for use for water disinfection inside a water tank.

The UV LEDs described herein emit ultraviolet light having a wavelength that will disrupt bacteria in order to disinfect the water being treated. In a specific example, the wavelength of the light emitted may be between about 220 nm to about 310 nm. In a particular embodiment, the wavelength of the light emitted may be between about 250-270 nm. In an even more particular embodiment, the wavelength of the light emitted may be a single mono wavelength of 254 nm.

When UV energy is absorbed by the reproductive mechanisms of bacteria and viruses, the genetic material (DNA/RNA) is rearranged so that they can no longer reproduce, killing the bacteria and eliminating the risk of disease. UV treatment thus disinfects water without adding disinfection chemicals.

Figure 2:
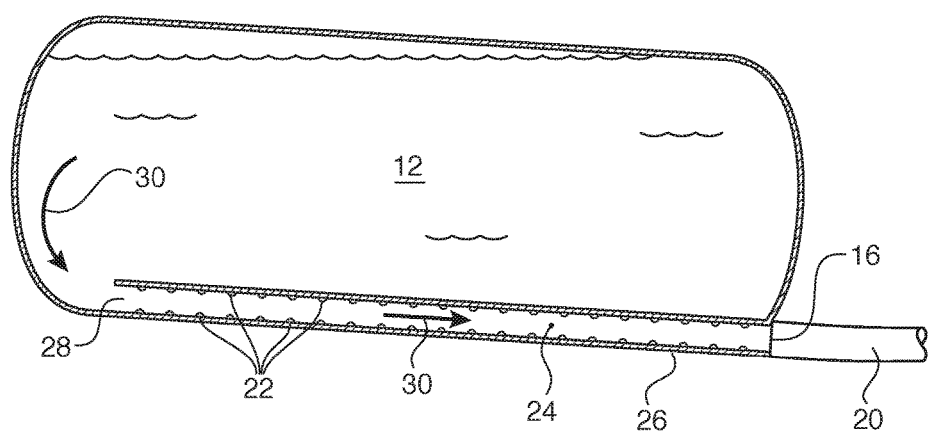
FIG. 2 shows one example of a UV treatment system installed along a drain outlet tube of a water tank.

The UV LEDs described herein are mounted or otherwise positioned so that they can emit light directly into water contained within the water tank 12. In use, UV rays are admitted and absorbed into the water stream. In one example illustrated by FIG. 2, an array 22 of UV LEDs may line a drain outlet tube 24. The drain outlet tube 24 may be provided along a lower portion or wall 26 of the water tank 12. An opening 28 at the mouth of the drain outlet tube 24 may receive water held in the water tank 12. As water passes through the drain outlet tube 24 in the direction illustrated by arrows 30, it is treated by the array 22 of UV LEDs prior to its exit at outlet 16. This causes all water exiting the water tank 12 to receive a strong dose of UV irradiation from the UV LEDs.

As illustrated, the water tank 12 may be installed at a slight angle so that gravity helps force water down along the drain outlet tube 24 and out the outlet 16. In order to prevent water pooling along a lower end portion/upper surface of the drain outlet tube 24, it is possible to provide one or more pumps within water tank 12 that force water up to the opening 28.

Figure 3:
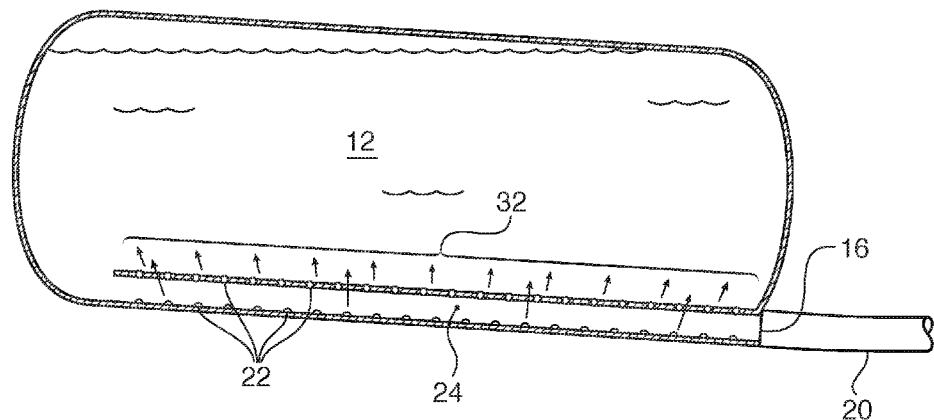
FIG. 3 shows the system of FIG. 2 with a transparent drain outlet tube.

In one example, it is possible for the drain outlet tube 24 to be transparent, such that some of the UV irradiation is also delivered out of the tube 24 and into the general store of water being held in the water tank 12. An example of this embodiment is illustrated by FIG. 3. The external radiation of UV light is illustrated by arrows 32.

Figure 4:
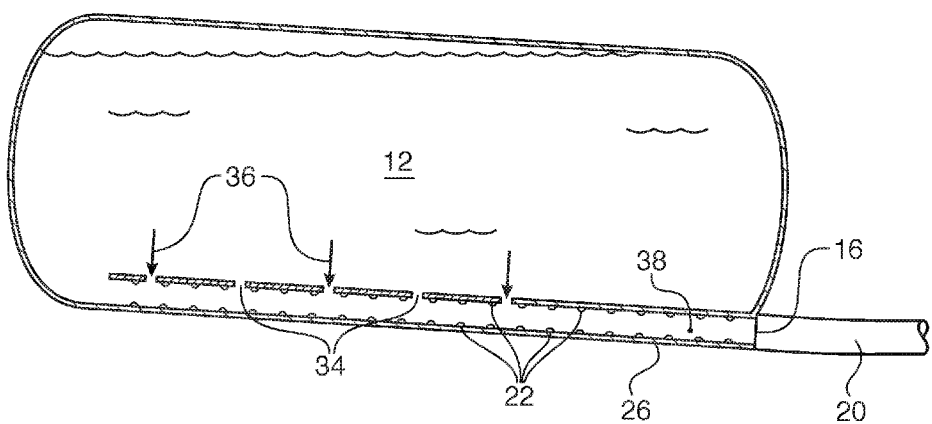
FIG. 4 shows the system of FIG. 2 with a drain outlet tube having one or more openings therein.

In another example illustrated by FIG. 4, the drain outlet tube 24 may be provided with one or more openings 34 along the tube length. These openings 34 allow water being held in the water tank 12 to flow into the drain outlet tube 24 along the various portions thereof. This water inflow is illustrated by arrows 36. One benefit of this embodiment may be that more water may be allowed to enter the drain outlet tube 24 more quickly. The lower wall 26 of the drain outlet tube 24 may be provided with an array 22 of UV LEDs, as described above. It is also possible to provide the portions of the drain outlet tube 24 without openings 34 as also having an array 22 of UV LEDs. In this example, an end portion 38 of the drain outlet tube 24 may be provided without any openings 34. This feature may help ensure that any water entering one of the openings 34 closer to the end portion 38 is still provided adequate UV water treatment prior to exit at outlet 16.

Figure 5:
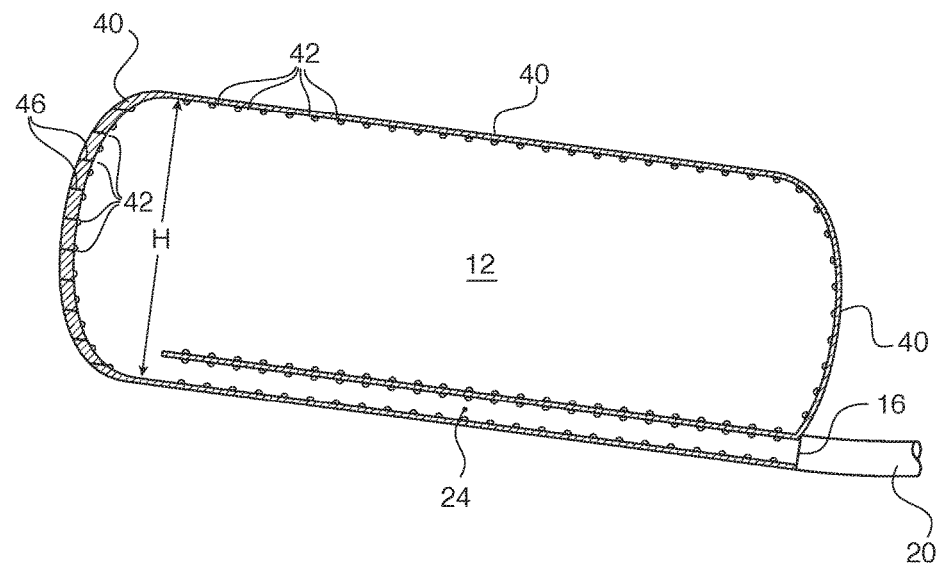
FIG. 5 shows one example of a UV treatment system installed along walls of a water tank.
Figure 6:
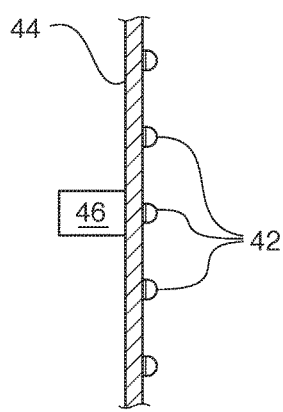
FIG. 6 shows an exemplary panel that may be used to install UV LEDs along walls of a water tank.

Additionally or alternatively to any of the above described options, FIG. 5 illustrated that one or more walls 40 of the water tank may have UV LEDs associated therewith. The UV LEDs 42 may be individual LEDs that are positioned along one or more walls 40. For ease of electrical connections, an alternate version provides a series of UV LEDs 42 positioned along a panel 44, as illustrated by FIG. 6. The panel 44 may have associated electrical connections and power options, illustrated schematically by reference numeral 46. In use, one or more panels 44 may be installed along one or more walls 40. The result is that UV irradiation reflects inwardly toward the water contained within the water tank 12.

In these examples, the UV LEDs 42 may communicate with one or more water level sensors 46. The water level sensors 46 may be positioned along various portions of the height H of the water tank. The one or more water level sensors 46 may relay information to the one or more UV LEDs 42 about whether or not the UV LED is in contact with water. As the level of water rises in the water tank 12 and submerses a particular UV LED 42 (or panel of UV LEDs), power to the UV LED (or panel) is turned on. If the water level sensor 46 senses that the UV LED is not in contact with water, the power may be switched off. In addition to saving power, this can prevent UV LEDs from warming too quickly or overheating. Alternatively, it may be possible that maintaining a UV LED that is not in contact with water in a powered condition may still provide potential disinfection treatment. For example, the UV LEDs may be angled downwardly so that their light may still be directed toward a lower water level in the water tank 12. It may be also possible that directing UV LED light to the interior tank walls 40 may help prevent accumulation of biofilm or other bacteria on the walls, even when water is not present.

Figure 7:
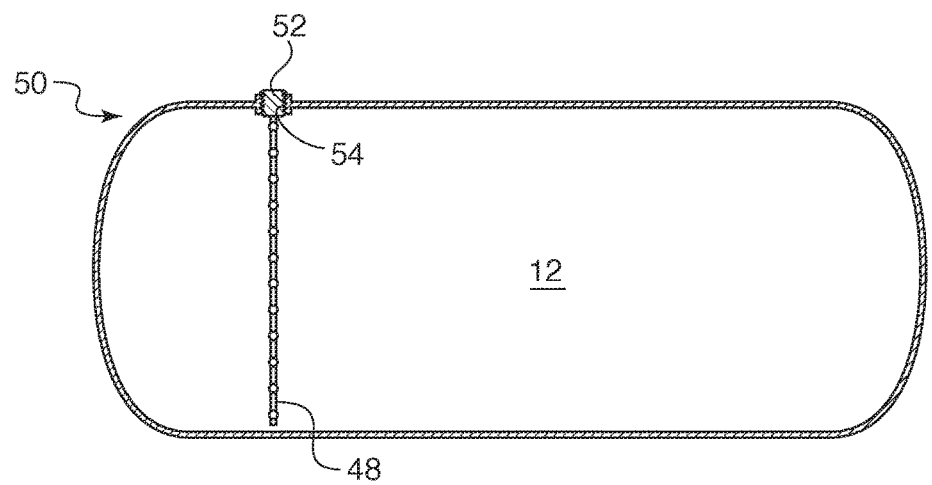
FIG. 7 shows one example of a UV treatment system installed along a UV LED string.
Figure 8:
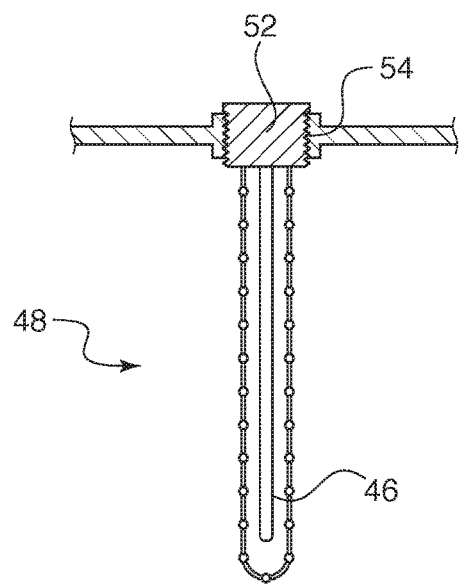
FIG. 8 illustrates one securement method for the UV LED string of FIG. 7.

Additionally or alternatively to any of the above described examples, it is also possible to provide one or more strings or panels of UV LEDs that are positioned in the water tank 12. FIG. 7 shows a single UV LED string 48 for simplicity, although it should be understood that multiple UV LED strings 48 in any number and any location may be used. As shown, a UV LED string 48 may be mounted or otherwise positioned with respect to an upper portion 50 of the water tank 12. In one example, the UV LED string 48 may have a cap 52 that is screwed into a threaded opening 54 or otherwise mounted with respect to a tank wall. This example is illustrated by FIG. 8. FIG. 8 also illustrates an optional water sensor 46 that may be provided within the UV LED string 48, which functions as described above. Although the figures illustrate the UV LED string 48 extending downwardly, it should be understood that the UV LED string 48 may extend horizontally through the water tank 12. The string 48 may be rigid or may be flexible, depending upon the tank size and requirements. These embodiments may be used in conjunction with one another or alternatively to one another.

Additionally or alternatively to any of the above described examples, it is also possible to provide a UV LED ring 56 at either the tank inlet 14, the tank outlet 16, or both. One example of this option is illustrated by FIG. 9. The UV LED ring 56 may be designed to be installed at the inlet 14 and/or the outlet 16 in order to treat water upon entry to the water tank 12 (if positioned at the inlet 14) and/or to treat water upon exit from the water tank 12 (if positioned at the outlet 16). In either or both option, the UV LED ring 56 may be provided with a series of UV LEDs around the perimeter or circumference of the ring 56, as illustrated by FIG. 10.

Additionally or alternatively, it is possible to provide a UV LED sheath 58 that can be positioned in the conduit 20 immediately prior to the inlet 14 and/or immediately following the outlet 16. One example is illustrated by FIG. 11. The positioning of the ring the 56 or the sheath 58 may be via friction fit, via adhesive, by a welding, via screw fit, via fasteners, or via any other appropriate securement system.

The above disclosure provides examples of the features sought to be protected by the below claims. It should be understood that changes and modifications, additions and deletions may be made to the structures and methods recited above and shown in the drawings without departing from the scope or spirit of the disclosure or the following claims.

What is claimed is:

1. A system for treating water contained in a potable water tank, comprising:
   a potable water holding tank configured to be installed on board a vehicle;
   one or more UV LEDs positioned within the potable water holding tank, the one or more UV LEDs positioned to deliver in-tank water treatment, prior to water leaving the holding tank, wherein the one or more UV LEDs are positioned along a drain outlet tube.

2. The system of claim 1, wherein the drain outlet tube comprises a transparent tube.

3. The system of claim 1, wherein the drain outlet tube comprises one or more openings along the drain outlet tube.

4. The system of claim 1, wherein the one or more UV LEDs are positioned along one or more walls of the water tank.

5. The system of claim 4, wherein the one or more UV LEDs are positioned on one or more panels installed with respect to the one or more walls.

6. The system of claim 1, wherein the one or more UV LEDs are positioned along a UV LED string.

7. The system of claim 6, wherein the UV LED string is mounted with respect to an upper portion of the water tank and extends vertically into the water tank.

8. The system of claim 6, wherein the UV LED string is mounted with respect to a sidewall of the water tank and extends horizontally into the water tank.

9. The system of claim 1, wherein the one or more UV LEDs are positioned along a UV LED ring positioned at the water tank inlet, the water tank outlet, or both.

10. The system of claim 1, wherein the one or more UV LEDs are positioned along a UV LED sheath positioned at the water tank inlet, the water tank outlet, or both.

11. A system for treating water contained in a potable water tank mounted on an aircraft, comprising:
   a potable water holding tank configured to be installed on board the aircraft;
   one or more UV LEDs positioned within the potable water holding tank, the one or more UV LEDs positioned to deliver in-tank water treatment, prior to water leaving the holding tank, wherein the one or more UV LEDs are positioned along a drain outlet tube.

* * * * *

UNITED STATES PATENT AND TRADEMARK OFFICE
CERTIFICATE OF CORRECTION

PATENT NO. : 10,266,426 B1
APPLICATION NO. : 15/835077
DATED : April 23, 2019
INVENTOR(S) : David Eugene Conrad et al.

Page 1 of 1

It is certified that error appears in the above-identified patent and that said Letters Patent is hereby corrected as shown below:

On the Title Page

In Item (54) and in the Specification, Column 1 Line 1 delete "PORTABLE" and insert
-- POTABLE -- therefor.

Signed and Sealed this
Eleventh Day of June, 2019

Andrei Iancu
*Director of the United States Patent and Trademark Office*